United States Patent
Morris et al.

(10) Patent No.: US 10,748,647 B2
(45) Date of Patent: *Aug. 18, 2020

(54) AUTOMATIC GENERATION OF AN EXECUTIVE SUMMARY FOR A MEDICAL EVENT IN AN ELECTRONIC MEDICAL RECORD

(71) Applicant: Microsoft Technology Licensing, LLC, Redmond, WA (US)

(72) Inventors: Daniel Scott Morris, Bellevue, WA (US); Desney S. Tan, Kirkland, WA (US); Lauren Gabrielle Wilcox-Patterson, Montclair, NJ (US); Gregory R. Smith, Bellevue, WA (US); Amy Kathleen Karlson, Bellevue, WA (US); Asta Jane Roseway, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 387 days.

This patent is subject to a terminal disclaimer.

(21) Appl. No.: 15/629,476

(22) Filed: Jun. 21, 2017

(65) Prior Publication Data

US 2017/0286601 A1   Oct. 5, 2017

Related U.S. Application Data

(63) Continuation of application No. 13/018,429, filed on Feb. 1, 2011, now Pat. No. 9,805,160.

(51) Int. Cl.
*G06F 7/00* (2006.01)
*G16H 10/60* (2018.01)
*G06Q 50/24* (2012.01)

(52) U.S. Cl.
CPC ............. *G16H 10/60* (2018.01); *G06Q 50/24* (2013.01)

(58) Field of Classification Search
CPC ........ G16H 10/60; G16H 80/00; G16H 40/67; G16H 10/20; G16H 50/30; G06Q 50/24; G06Q 10/10; G06Q 30/0269
See application file for complete search history.

(56) References Cited

U.S. PATENT DOCUMENTS 7,395,215 B2   7/2008   Grushka
8,849,830 B1 *  9/2014  Srinivasan ............ G06F 16/951
                                                  707/740

(Continued)

OTHER PUBLICATIONS

Patrick, et al., "A Cascade Approach to Extracting Medication Events", Retrieved at << http://www.aclweb.org/anthology/U/U09/U09-1014.pdf >>, Proceedings of the Australasian Language Technology Association Workshop, 2009, pp. 1-5.

(Continued)

*Primary Examiner* — Azam M Cheema
(74) *Attorney, Agent, or Firm* — Medley, Behrens & Lewis, LLC

(57) ABSTRACT

Described herein are technologies pertaining to automatic generation of an executive summary (explanation) of a medical event in an electronic medical record (EMR) of a patient. A medical event in the EMR is automatically identified, and a search is conducted over a document corpus based upon the identified medical event. A document retrieved as a result of the search is analyzed for a portion of text to act as an executive summary for the medical event. Each portion of text in the document is assigned a score, and the portion of text assigned the highest score is utilized as the executive summary for the medical event.

20 Claims, 7 Drawing Sheets

(56) References Cited

U.S. PATENT DOCUMENTS

| | | | |
|---|---|---|---|
| 9,805,160 B2* | 10/2017 | Morris | G16H 10/60 |
| 2002/0082868 A1 | 6/2002 | Pories et al. | |
| 2005/0010446 A1 | 1/2005 | Lash et al. | |
| 2005/0108001 A1 | 5/2005 | Aarskog | |
| 2007/0061171 A1* | 3/2007 | Ash | G16H 15/00 |
| | | | 705/3 |
| 2008/0021738 A1 | 1/2008 | Komiya et al. | |
| 2008/0077570 A1 | 3/2008 | Tang et al. | |
| 2008/0249761 A1 | 10/2008 | Easterly | |
| 2009/0024411 A1 | 1/2009 | Albro et al. | |
| 2009/0083231 A1 | 3/2009 | Eberholst et al. | |
| 2009/0112627 A1* | 4/2009 | Berkman | G06Q 50/22 |
| | | | 705/3 |
| 2010/0076780 A1* | 3/2010 | Mahesh | G06Q 10/10 |
| | | | 705/2 |
| 2010/0131434 A1 | 5/2010 | Magent et al. | |
| 2010/0179827 A1 | 7/2010 | McCallie et al. | |
| 2010/0198571 A1 | 8/2010 | Morris et al. | |
| 2011/0077968 A1 | 3/2011 | Kelly et al. | |
| 2011/0137682 A1* | 6/2011 | Hoffman | G06Q 50/22 |
| | | | 705/3 |
| 2012/0129572 A1 | 5/2012 | Johnstone et al. | |
| 2012/0197876 A1 | 8/2012 | Morris et al. | |

OTHER PUBLICATIONS

Tschirley, et al., "Patient-Oriented Segmentation and Visualization of Medical Data", Retrieved at << http://citeseerx.ist.psu.edu/viewdoc/download?doi=10.1.1.3.9091&rep=rep1&type=pdf >>, In Proceedings of CGIM computer Graphics and Imaging, 2002, pp. 1-6.

Bickmore, et al., "Taking the Time to Care: Empowering Low Health Literacy Hospital Patients with Virtual Nurse Agents", Retrieved at << http://www.ccs.neu.edu/home/laurap/pub/CHI09.VirtualNurse.pdf >>, CHI Conference on Human Factors in Computing Systems, Apr. 4-9, 2009, pp. 1-10.

Deléger, et al., "Extracting Lay Paraphrases of Specialized Expressions from Monolingual Comparable Medical Corpora", Retrieved at << http://www.limsi.fr/~pz/FTPapiers/Deleger_BUCC2009.pdf >>, Second Workshop on Building and Using Comparable Corpora: from Parallel to Non-parallel Corpora, Aug. 6, 2009, pp. 2-10.

Dimarco, et al., "Authoring and Generation of Individualized Patient Education Materials", Retrieved at << http://www.cs.uwaterloo.ca/~cdimarco/pdf/publications/JITH2008.pdf >>, Journal on Information Technology in Healthcare, 2008, pp. 63-71.

Elhadad, et al., "Mining a Lexicon of Technical Terms and Lay Equivalents", Retrieved at << http://people.dbmi.columbia.edu/noemie/papers/bionlp07.pdf >>, ACL BioNLP Workshop, 2007, p. 8.

Jones, Ray., "The Role of Health Kiosks in 2009: Literature and Informant Review", Retrieved at << http://www.mdpi.com/1660-4601/6/6/1818/pdf>>, International Journal of Environmental Research and Public Health, vol. 06, No. 6, 2009, pp. 1818-1855.

Portet, et al., "Automatic Generation of Textual Summaries from Neonatal Intensive Care Data", Retrieved at << http://citeseerx.ist.psu.edu/viewdoc/download?doi=10.1.1.157.8444&rep=rep1&type=pdf >>, Artificial Intelligence, vol. 173, No. 7-8, May 2009, pp. 1-28.

Pratt, et al., "Personal Health Information Management", Retrieved at << http://faculty.washington.edu/wpratt/Publications/CACMp51-pratt.pdf >>, Communications of the ACM, vol. 49, No. 1, Jan. 2006, pp. 51-55.

Tang, et al., "The Missing Link: Bridging the Patient-Provider Health Information Gap", Retrieved at << http://senweb03.senate.ca.gov/committee/standing/health/Tang_Health_Affairs.pdf>>, Health Affairs, vol. 24, No. 5, 2005, pp. 1290-1295.

Wilcox, et al., "Designing Patient-Centric Information Displays for Hospitals", Retrieved at << http://research.microsoft.com/en-us/um/redmond/groups/cue/publications/WilcoxPatientDisplaysCHI2010.pdf >>, CHI Conference on Human Factors in Computing Systems, Apr. 10-15, 2010, pp. 10.

"Final Office Action for U.S. Appl. No. 13/018,429", dated Nov. 28, 2016, 44 pages.

"Response to the Final Office Action for U.S. Appl. No. 13/018,429", Filed Date: May 29, 2017, 14 pages.

"Response to the Final Office Action for U.S. Appl. No. 13/018,429", Filing date: May 19, 2015, 16 pages.

"Final Office Action for U.S. Appl. No. 13/018,429", dated Dec. 31, 2014, 35 pages.

"Response to the Office Action for U.S. Appl. No. 13/018,429", dated Sep. 19, 2016, 18 pages.

"Office Action for U.S. Appl. No. 13/018,429", dated Mar. 17, 2016, 40 pages.

"Office Action for U.S. Appl. No. 13/018,429", dated Apr. 3, 2014, 28 pages.

"Response to the Office Action for U.S. Appl. No. 13/018,429", Filed Date: Sep. 12, 2014, 13 pages.

* cited by examiner

AUTOMATIC GENERATION OF AN EXECUTIVE SUMMARY FOR A MEDICAL EVENT IN AN ELECTRONIC MEDICAL RECORD

RELATED APPLICATION

This application is a continuation of U.S. patent application Ser. No. 13/018,429, filed on Feb. 1, 2011, and entitled "AUTOMATIC GENERATION OF AN EXECUTIVE SUMMARY FOR A MEDICAL EVENT IN AN ELECTRONIC MEDICAL RECORD", the entirety of which is incorporated herein by reference.

BACKGROUND

Active involvement by patients inw their own health care has been shown to lead to greater overall patient satisfaction, which in turn results in greater trust and compliance. Increased tolerance for discomfort, reduced stress, reduced medical complications, enhanced placebo effects, and increases in overall benefit to quality of care depends significantly on patients being well informed about the care that they are receiving. Today, patients have several informational resources at their disposal to become well-informed about their care. For example, physicians typically explain symptoms, diagnoses, conditions, and treatments to patients verbally when the physician is meeting with the patient. Unfortunately, with increasing stresses on the healthcare system, in-person explanations may not meet all the informational needs of the patient. Additionally, these in-person explanations are not always readily accessible as physicians become more and more in demand.

Educational materials that can be accessed by individuals regarding procedures undertaken with respect to the patient in the past and medications taken by the patient in the past provide additional information for the patient about the care that she is receiving or expects to receive. Oftentimes, these materials can be overwhelming to patients experiencing emotional distress, as is often the case in hospital environments. Furthermore, in many instances, patients will lack literacy with respect to certain medical terms. Further, information packets are rarely tailored to a specific patient. Also, traditional media for delivering information to patients (e.g., paper) makes dynamic and customized delivery of medical information difficult.

In addition to the aforementioned information sources, in the relatively recent past electronic medical records (EMRs) have been made available to patients, thereby allowing patients to have unprecedented levels of access to their own medical data. Despite such availability, however, patients often remain uninformed about tests and procedures conducted during clinical visits, leaving them ill-equipped to participate in important medical decisions. This discrepancy is largely a consequence of the structure and terminology used in EMRs, which are designed for clinicians and administrators rather than for patients.

SUMMARY

The following is a brief summary of subject matter that is described in greater detail herein. This summary is not intended to be limiting as to the scope of the claims.

Described herein are various technologies pertaining to the automatic generation of an executive summary for medical events that are included in an electronic medical record (EMR) of an individual. The executive summary can be selected/constructed such that the individual can be provided with some high-level knowledge pertaining to the medical event in the EMR. As will be appreciated by one skilled in the art, an electronic medical record can include several medical events, wherein a medical event can be an identity of a test that has been performed on the individual or is scheduled to be performed on the individual, a medication that has been prescribed to the individual or has been ingested by the individual, a diagnosis of an ailment being experienced by the individual, a treatment that is to be performed on the individual, amongst other known medical events. At least one medical event in the electronic medical record of the individual can be automatically identified and selected. For example, a list can be created of known medical events that are commonly included in EMRs, and this list of known medical events can be compared with the contents of the EMR of the individual. If a medical event in the EMR is found to be matching a medical event in the predefined list of medical events, such medical event in the EMR can be identified, and an executive summary/explanation for the medical event can be automatically constructed/extracted as described below.

Subsequent to the at least one medical event being identified in the EMR of the individual, such medical event can be utilized to perform a search over a document corpus. Pursuant to an exemplary embodiment, the document corpus may be the World Wide Web, and a general-purpose search engine can be commissioned to search the World Wide Web based at least in part upon the at least one medical event identified in the EMR. Using this approach, the general-purpose search engine can retrieve a plurality of documents that are believed to be germane to the at least one medical event in the EMR of the individual. Some top threshold number of web pages retrieved by the general-purpose search engine can be analyzed for generation of an executive summary for the at least one medical event. For instance, a top 10 search results retrieved by the general-purpose search engine can be analyzed. Each of these web pages may include a plurality of portions of text, where a portion of text may be a sentence, a paragraph, a phrase, some threshold number of words or characters, etc.

Scores can be assigned to each portion of text in the web pages being considered for generation of the executive summary, wherein the scores can be generated based at least in part upon one or more features corresponding to be portions of text and/or other content in the EMR of the individual. Various exemplary features that can be utilized to assign scores to portions of text are described in greater detail below. Additionally, it will be understood contents of the EMR of the individual other than the medical event identified can be indicative of the context of the medical event. For instance, the meaning of a medical event may depend upon what illnesses the individual has been diagnosed with. In a particular example, an explanation of a type of medicine that has prescribed to an individual may depend upon a diagnosis corresponding to the individual, such that executive summary for the medical event (for the particular individual) should depend upon the diagnosis.

While the above has described a general-purpose search engine as locating web pages, is to be understood that any suitable document corpus can be utilized in connection with generating executive summaries. For instance, a hospital may maintain a document corpus describing medical events, and such document corpus can be searched over utilizing any suitable search technology. In yet another example, physician-generated descriptions of different medical events can be retained in a data repository, and such physician-generated explanations of medical events can be searched in connection with generating the executive summary. A portion of text from at least one of the documents can be extracted and electronically associated with the at least one medical event in the EMR of the individual. This portion of text can be found to be the "best" portion of text for describing the at least one medical event in the EMR of the individual. It is to be understood, however, that rather than extracting a portion of text, an executive summary for a medical event can be constructed from multiple different portions of text, and the resulting, constructed text can be an executive summary for the at least one medical event in the EMR of the individual.

Once the executive summary has been extracted from the at least one document located during the search of the document corpus, the executive summary can be electronically associated with the at least one medical event in the EMR of the individual. For instance, a hyperlink can be added in connection with the medical event in the EMR, and selection of such hyperlink or hovering over the hyperlink can cause the executive summary for the medical event to be displayed to the individual that is perusing the EMR. In another example, subsequent to the EMR being updated by a physician with a medical event, a computer screen in a medical facility can be configured to display the medical event as well as an executive summary for the medical event. If a physician prescribes a new medication to an individual, for example, a computer screen in the office of the physician can display the medication that is being prescribed to such individual as well as an executive summary that explains the purpose of the medication for that individual. Other delivery mechanisms for displaying the automatically generated executive summary for the at least one medical event in the EMR the individual are also contemplated. For instance, presentation of the at least one medical event from the EMR of the individual and a corresponding executive summary can be undertaken on a portable computing device of the individual. That is, the hospital can configure a communication system to communicate with a mobile telephone of the individual in the form of a text message or picture message, such that the individual can be provided with an executive summary for a medical event to her mobile telephone. In another example, the individual may consent to having the medical event and the corresponding executive summary published to an information feed of the individual. Such information feed may be a social network feed that is viewable only to the individual when such individual logs in to her account. Furthermore, the individual can consent to causing the medical event and corresponding executive summary to be published to electronic accounts of friends and family of the individual.

Other aspects will be appreciated upon reading and understanding the attached figures and description.

DETAILED DESCRIPTION

Figure 1:
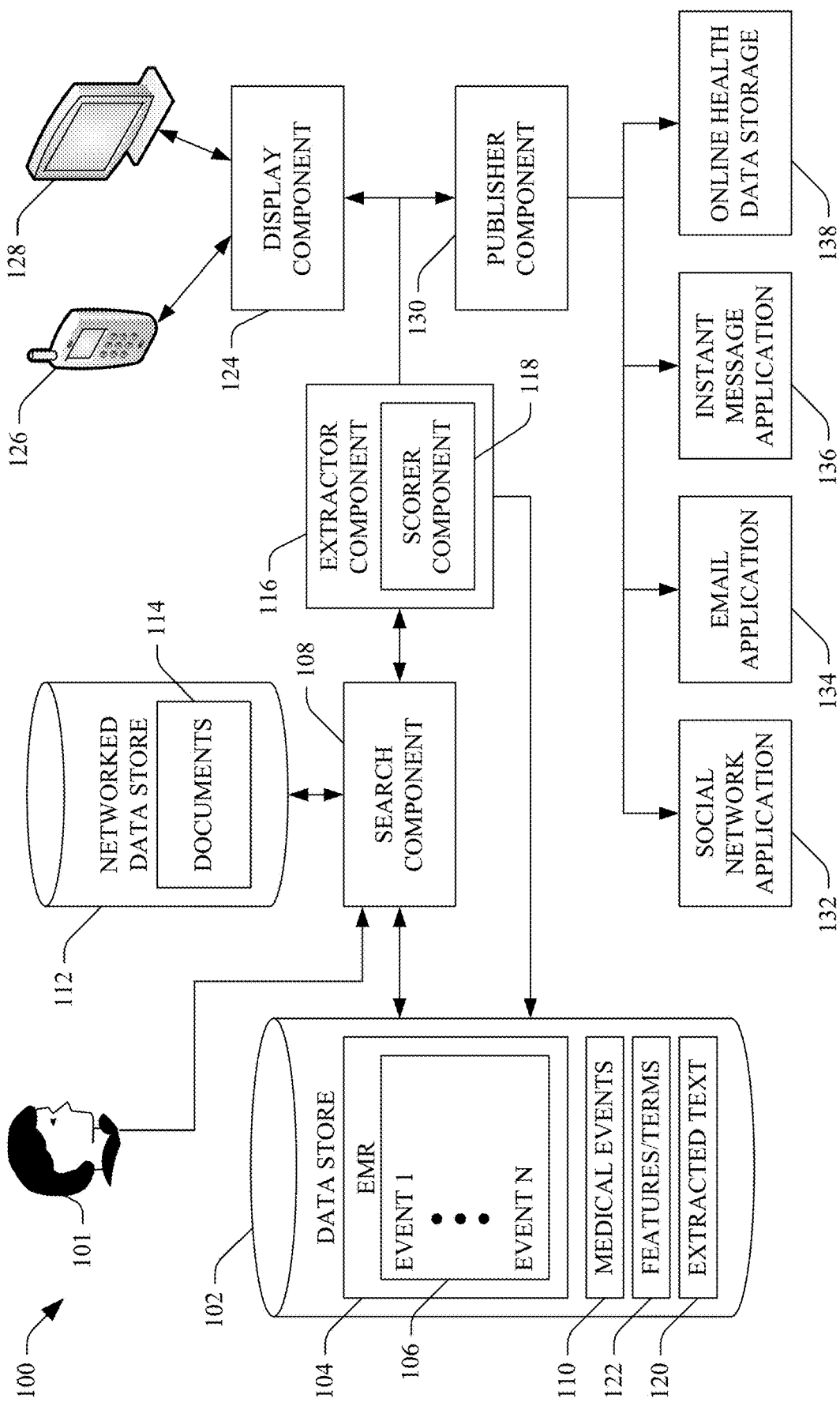
FIG. 1 is a functional block diagram of an exemplary system that facilitates automatically generating an executive summary for a medical event in an electronic medical record of an individual.

Various technologies pertaining to automatically generating an executive summary/executive explanation for a medical event in an electronic medical record of an individual will now be described with reference to the drawings, where like reference numerals represent like elements throughout. In addition, several functional block diagrams of exemplary systems are illustrated and described herein for purposes of explanation; however, it is to be understood that functionality that is described as being carried out by certain system components may be performed by multiple components. Similarly, for instance, a component may be configured to perform functionality that is described as being carried out by multiple components. Additionally, as used herein, the term "exemplary" is intended to mean serving as an illustration or example of something, and is not intended to indicate a preference.

With reference to FIG. 1, an exemplary system 100 that facilitates automatic generation of an executive summary for a medical event in an electronic medical record (EMR) of an individual 101 is illustrated. The system 100 comprises a data store 102 that retains an EMR 104 of the individual 101, wherein the EMR 104 comprises a plurality of medical events 106. The medical events 106, for example, can include medications prescribed to the individual 101, treatments prescribed to the individual 101, diagnoses of illnesses or ailments corresponding to the individual 101, medical tests that are to be performed or have been performed on the individual 101, amongst other medical events. Pursuant to an example, the data store 102 may be a data store residing on a computing device owned or managed by a hospital facility, and/or maybe a computing device that is owned and/or operated by the individual 101.

The system 100 further comprises a search component 108 that can access the data store 102 and can analyze the EMR 104. The data store 102 may also include a plurality of predefined medical events 110, wherein such medical events 110 may be included in EMRs of patients. Pursuant to an example, the search component 108 can compare the medical events 106 in the EMR 104 of the individual with the predefined medical events 110. That is, the search component 108 can ascertain whether the EMR 104 includes any of the predefined medical events 110. If the search component 108 finds that the EMR 104 includes a medical event that is in the predefined medical events 110, then the search component 108 can perform a search for documents based at least in part upon the identified medical event.

With more particularly, the system 100 can also comprise a networked data store 112 that is accessible to the search component 108 by way of some suitable network. For example, the network may be the Internet, such that the search component 108 can perform a search for documents by way of an Internet connection. In another example, the network may be an intranet that is managed by a medical facility, such as a hospital, a doctor's office, or the like. The networked data store 112 comprises a plurality of documents 114 that are germane to one or more of the predefined medical events 110. Pursuant to an example, the documents 114 may be consumer-facing web pages, and the search component 108 can be a general-purpose search engine that searches over the web pages utilizing the medical event as a query or a part of a query. In another example, the documents 114 may be a collection of documents maintained by a medical facility that describe medical events that may be included in EMRs of patients In such a case, the search component 108 can search over this proprietary collection of documents utilizing, for instance, a medical event in the EMR as a search term or query.

Based at least in part upon a search over the documents 114, the search component 108 can retrieve at least one document from the documents 114, wherein the at least one document relevant to the identified medical event in the EMR 104 of the individual 101. Pursuant to an example, the search component 108 can be a general-purpose search engine and can retrieve a most highly ranked document or threshold number of documents from the World Wide Web. The most highly ranked document or documents may then be subject to analysis to locate or construct an executive summary for the medical event found in the EMR 104.

The system 100 further comprises an extractor component 116 that is in communication with the search component 108. The extractor component 116 receives the least one document retrieved by the search component 108 subsequent to the search component 108 performing the search using the medical event as the query or search term. The extractor component 116 may then extract a portion of text from at least one document retrieved by the search component 108, and can cause such a portion of text to be electronically associated with the medical event in the EMR 104 as an executive summary of such medical event. With more particularity, the extractor component 116 can comprise a scorer component 118 that assigns scores to portions of text in the at least one document retrieved by the search component 108. As used herein, the term "portion of text" can refer to a sentence in the document retrieved by the search component 108, a paragraph in the document retrieved by the search component 108, a phrase in the document retrieved by the search component 108, a threshold number of words or characters in the document retrieved by the search component 108, etc. A portion of text, as will be understood, is less than the entirety of text included in the document retrieved by the search component 108.

The scorer component 118 can analyze each portion of text in the document retrieved by the search component 108 and can assign scores to each portion of text in the document based at least in part upon one or more features corresponding to the portions of text in the document as well as other content of the EMR 104. Exemplary features that can be utilized by the scorer component 118 in connection with assigning scores to portions of text in the document retrieved by the search component 108 will be described in detail below. Furthermore, as mentioned, the scorer component 118 can consider other content in the EMR 104 of the individual in connection with assigning scores to portions of text in the document retrieved by the search component 108. For instance, the meaning or purpose of one medical event in the EMR 104 may be based at least in part upon the meaning or purpose of another medical event in the EMR 104 of the individual 101. Pursuant to a particular example, the purpose or meaning of the prescription of a certain type of medication can vary depending upon an illness or ailment of the individual as indicated in the EMR 104. Therefore, for instance, an individual suffering from diabetes will have a different utilization for a particular medication than an individual suffering from emphysema, for example, even though the same medication may be prescribed to both individuals. It can therefore be ascertained that content of the EMR 104 can influence the meaning of medical events in the EMR 104, as the content of the EMR 104 can provide context for use in connection with generating an executive summary of a medical event.

Pursuant to an example, the portion of text from the at least one document retrieved by the search component 108 that has been assigned the highest score by the scorer component 118 can be extracted as extracted text 120, and the extracted text 120 can be utilized as the executive summary for the medical event in the EMR 104. Specifically, extractor component 116 can cause the extracted text 120 to be retained in the data store 102 in association with the medical event in the EMR 104. As indicated previously, the data store 102 can comprise features and terms 122 that can be utilized by the scorer component 118 in connection with assigning scores to portions of text in documents retrieved by the search component 108. Such features and terms 122 can include, but are not limited to including, length of a sentence, whether a sentence includes a predefined symptom, whether a sentence includes a predefined organ, whether a sentence includes a predefined biological system, whether a sentence includes a predefined body part, whether a sentence includes a predefined diagnosis, whether a sending sentence includes a predefined acronym, whether a sentence includes eight predefined medical term, a number of medical terms in a sentence, whether a sentence includes words found elsewhere in the electronic medical record of the individual, etc. Additional features/terms that can be included in the data store 102 and utilized by the scorer component 118 when assigning scores to portions of text in documents retrieved by the search component 108 will be provided herein.

Once the extractor component 116 has created the executive summary for the medical event in the EMR 104, it may be desirable to present such medical event together with the executive summary to the individual. To that end, the system 100 can optionally comprise a display component 124 that is configured to cause computing devices to display the executive summary of the medical event together with such medical event to the individual 101. In an example, the display component 124 can be configured to cause the medical event and corresponding executive summary to be transmitted to a mobile computing device 126, such as a mobile telephone, a mobile multimedia device etc., and such mobile computing device 126 can display the medical event and corresponding executive summary to the individual 101. Pursuant to a particular example, the display component 124 can cause the medical event and corresponding executive summary to be displayed on the portable computing device 126 as a text message, a picture message, as a web page in a browser executing on the portable computing device 126, or other suitable format. For instance, the individual 101 may be in the office of the physician and may be prescribed a particular medication by the physician. The physician can update the EMR 104 of the individual with this new medical event (prescribing of the medicine). Responsive to the EMR 104 being modified, the search component 108 can search the documents 114 in the networked data store 112 to locate documents that are relevant to such medical event. The extractor component 116 may then generate the executive summary as described above, and the display component 124 can cause the executive summary to be transmitted to the mobile computing device 126 of the user for display thereon. Therefore, the individual 101 can readily be provided with information that is important to the health care of such individual 101.

In another example, the medical facility may have a display screen 128 in a waiting room in which the individual resides, and the display component 124 can be configured to display the medical event and corresponding executive summary to the individual 101 on the display screen 128. In another example, the display screen 128 can be a portion of a bedside computing device for the individual 101. Thus, the individual 101 can be provided with information about medical events included in the EMR 104 of the individual 101 at the request of the individual 101 and/or upon the EMR 104 being modified.

Moreover, in an exemplary embodiment, the individual 101 may wish to obtain additional information regarding data that is initially presented to such individual 101 by way of the display component 124. For example, at least a portion of text that is included in an executive summary of a medical event depicted to the individual can be displayed in the form of a hyperlink, and upon selecting the hyperlink additional information can be provided to the individual 101. For instance, a web page can be accessed upon selecting the hyperlink. In another example, hyperlinked text may be another medical event, and selecting the hyperlink can cause a new executive summary for the medical event to be generated as described above.

Still further, the display component 124 can be configured to present additional information to the individual 101 together with text extracted by the extractor component 116. This information can include, but is not limited to including, information about the care team (that includes at least one care giver) assigned to the individual 101, communications from someone in the care team assigned to the individual 101, a medication prescribed to the individual 101, a test performed on the individual 101, a result from a test performed on the individual 101, information the individual 101 may be waiting on, etc. At least some of this data can be presented in lay-person terms through text extraction techniques described above.

In some situations, the individual 101 may wish to publish the medical event and corresponding executive summary for later viewing and/or viewing by others such as friends and family of the individual 101. Therefore, the system 100 can optionally comprise a publisher component 130 that is in communication with the extractor component 116, wherein the publisher component 130 can receive the medical event and corresponding executive summary and can publish such medical event and executive summary to an application or system specified by the individual 101. For instance, the individual may have an account with a particular social networking application wherein, for instance, such application may be configured to broadcast a relatively small amount of text to specified friends and family of the individual 101 and/or to a feed that can be seen only by the individual 101. In another example, the social network application 132 may be utilized to receive information from contacts of the individual and post data to contacts of the individual 101. In either of these examples, the individual 101 can specify that she wishes that the medical event and corresponding executive summary be published to an information feed corresponding to the social network application 132. When the individual 101 logs into the social network application 132 and select the information feed, the individual 101 can be provided with the medical event and executive summary. This may be particularly beneficial in many situations, as oftentimes individuals will log into their social network applications and leave such applications executing on their computing devices, including mobile devices. Accordingly, if the individual 101 is logged into the social network application 132, such individual 101 can quickly be provided with information pertaining to their visits to a healthcare facility (including the medical event and corresponding executive summary). In addition, in some situations, the individual 101 may wish to share what has happened at the medical facility with friends or family. Accordingly, with the consent of the individual 101, the individual 101 can cause the medical event and corresponding executive summary to be published to information feeds of specified friends and family of the individual. Accordingly, the individual 101 can inform selected friends and family of medical information pertaining to the individual in an efficient manner.

In another exemplary embodiment, the publisher component 130 can interface with an e-mail application 134. In this embodiment, the individual 101 can authorize the publisher component 130 to cause an e-mail to be transmitted to selected contacts of the individual 101 or the individual herself, wherein such e-mail can include the medical event and a corresponding executive summary.

In yet another exemplary embodiment, the publisher component 130 can interface with an instant message application 136, such that the medical event and corresponding executive summary is transmitted as an instant message to an identified contact of the individual. The instant message can be transmitted to individuals that are currently online and/or can be transmitted as an off-line message to specified contacts of the individual 101.

In still yet another exemplary embodiment, the publisher component 130 can interface with online health data storage 138. Currently, some online services are offering space to retain personal health records. This allows the individual 101 to go to a single place by way of an Internet browser to review data corresponding to their personal health. A personal health record can be distinguished from an EMR, as an EMR is retained at a medical facility while a personal health record is owned by the individual 101 and managed by the individual 101. The publisher component 130 can be configured to automatically publish or cause to be stored in the online health data storage 138 one or more medical events in the EMR 104 of the individual together with the corresponding executive summaries. Therefore, the individual 101 can log into the online health data storage 138 to review their personal health record, which can include executive summaries of medical offense in the EMR 104 of the individual 101.

While several examples of that provided herein for displaying or publishing a medical event and corresponding executive summary of an individual, it is to be understood that any suitable manner for presenting this type of information to the individual or specified contacts of the individual is contemplated by the inventors and is intended to fall under the scope of the hereto-appended claims. For instance, the executive summary and corresponding medical event can be provided to the individual by way of a printing application that can print out such executive summary for presentment to the individual.

Furthermore, the embodiments described herein have related to identifying a single medical event in the EMR 104 of the individual and generating an executive summary for such identified event. It is to be understood, however, that the system 100 can be configured to generate executive summaries for each medical event that is located in the EMR 104 of the individual 101. The individual 101 may then pick and choose which medical event and corresponding executive summaries to have displayed to the individual 101 and/or published by way of the publisher component 130.

Furthermore, it is to be understood that the individual 101 can provide the search component 108 with additional information for utilization when performing a search for documents germane to the medical events in the EMR 104. For instance, the individual 101 may wish to obtain information about a specific event in the EMR 104. In this case, the individual 140 can provide the search component 108 explicitly with the name of a medical event, and the search component 108 can locate one or more documents from the networked data store 112 based at least in part upon the information provided by the individual 101. Additionally or alternatively, information provided by the individual 101 can be utilized to supplement a query automatically generated by the search component 108. That is, the individual 101 can provide a specific query to be performed by the search component 108. This information provided by the individual can also be utilized by the extractor component 116 when extracting a portion of text from at least one document retrieved by the search component 108. In an example, data provided by the individual 101 can be included as a feature/term that is contemplated by the scorer component 118 when assigning scores to portions of text in documents retrieved by the search component 108. For example, if a portion of text scored by the scorer component 118 includes terms that were explicitly provided by the individual 101, such portions of text can be provided with higher scores than portions of text that do not include such terms.

While the discussion presented above relates to utilizing an extracted portion of text and labeling such extracted portion of text from a document as the executive summary for a medical event, it can be ascertained that other technologies can be employed in connection with automatically generating the executive summary for an identified medical event in the EMR 104 of the individual 101. For instance, rather than extracting text from one or more documents retrieved by the search component 108, the extractor component 116 make be configured with technology that allows construction of an executive summary from various different portions of one or more documents retrieved by the search component 108. In an exemplary embodiment, the extractor component 116 can be configured to pick and choose words in different sentences of documents retrieved by the search component 108 and can generate an executive summary that is made up of such words from the different sentences. Additionally, it is to be understood that a physician (or other suitable medical professional) can access the executive summary output by the extractor component 116 and can make any suitable alterations that the physician desires. Thus, the system 100 supports manual intervention by a medical professional on a case-by-case basis if desired.

Still further, it is to be understood that the privacy of the individual 101 is of utmost importance. Accordingly, prior to the search component 108 being authorized to analyze the EMR 104 of the individual 101, such individual 101 must provide explicit consent to the automatic generation of executive summaries for medical events in the EMR 104. Furthermore, the executive summaries and medical events are not displayed or presented to others without the explicit consent of the individual 101. Furthermore, when data from the EMR 104 of the individual 101 is utilized to perform a search or transmitted to other computing devices, such data can be removed from the EMR 104 that explicitly identifies the individual 101 and/or data can be encrypted during transmission such that the data can be reviewed only upon entering a certain username and password or having some cryptographic key being resident on a computing device.

Figure 2:
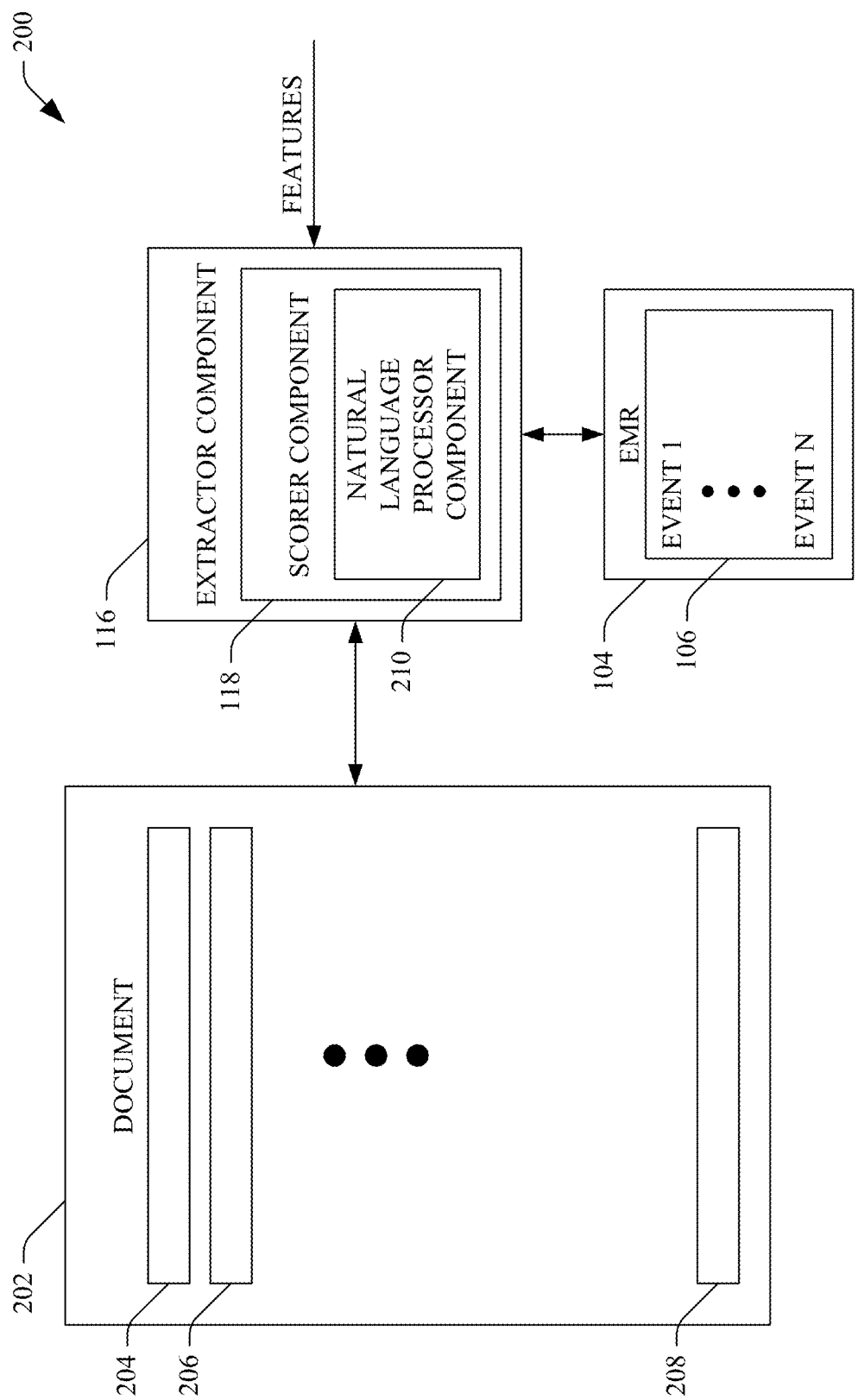
FIG. 2 is a social block diagram of an exemplary system that facilitates assigning scores to portions of text in a document in connection with automatically generating an executive summary for a medical event in an electronic medical record of an individual.

With reference now to FIG. 2, an exemplary system 200 that facilitates automatic generation of an executive summary for a medical event in an electronic medical record of an individual is illustrated. The system 200 comprises the extractor component 116, which can analyze a document 202 that has been retrieved by the search component 108. The document 202 comprises a plurality of portions of text 204-208. These portions of text 204-208 can be sentences, paragraphs, phrases, or some threshold number of words or characters. As the document 202 was retrieved by the search component 108, the document 202 includes information that is relevant to a medical event in the EMR 104 of the individual.

The scorer component 118, as indicated above, is configured to assign scores to each of the portions of text 204-208 in the document 202. The scorer component 118 assigns such scores based at least in part upon one or more features corresponding to the portions of text 204-208 in the document 202, content of the EMR 104, and/or explicitly provided information from an individual. In connection with assigning scores to the portions of text 204-208 in the document 202, the scorer component 118 can include a natural language processor component 210 that utilizes natural language processing techniques to ascertain semantic meaning of portions of text in the document 202.

As indicated previously, the scorer component 118 can consider various features when assigning scores to portions of text in documents in connection with selection a portion of text to utilize as an executive summary for a medical event. Below are several exemplary features that can be considered by the scorer component 118. It is to be understood, however, that these features are not an exhaustive set, and other features are contemplated by the inventors and are intended to fall under the scope of the hereto-appended claims.

Provided first is a list of features that can decrease the score assigned by the scorer component 118 to a portion of text in the document 202 being analyzed by the scorer component 118. In other words, these features can indicate that the portion of text being considered may be a poor executive summary (explanation) for a medical event. These features are not absolute, but can be combined by the scorer component 118 to score and rank candidate portions of text in the document 202.

A first feature that can cause the scorer component 118 to decrease a score assigned to a portion of text is when a portion of text is applicable only to medical histories or demographics that are not consistent with the current patient (as indicated in the EMR 104 of the individual). In an example, the explanation "diabetics and others at risk for developing kidney disease may be monitored for small amounts of protein in your urine by performing a microalbumin test" is irrelevant to an individual who does not have diabetes (as indicated in the EMR 104).

Another exemplary feature that can cause the scorer component 118 to decrease a score assigned to a portion of text is when medical terminology is included in a portion of text but not explained. An exemplary sentence that includes medical terminology that is not explained is as follows: "Most doctors use the plasma concentrations of the waste substances of creatine and urea, as well as electrolytes, to determine renal function." An exception to such feature is the use of acronyms that can be expanded but wouldn't require further explanation (shorthand for colloquial terms) or could be expanded based on existing dictionaries, such as RBC or Rx.

Another exemplary feature that can cause the scorer component 118 to decrease a score assigned to a portion of text is when the portion of text lacks diagnostic reasoning terminology, which are generally sentences that explain a method of administration, scientific background, or indicators for a test, but not a diagnostic value. An example of such a sentence is "the GFR can be determined by injecting insulin into the plasma."

Yet another exemplary feature that can cause the scorer component 118 to decrease a score assigned to a portion of text is when the portion of text (sentence) depends heavily on relationships with other tests not described in the sentence. An exemplary sentence of this sort is as follows: "the creatine test is ordered frequently as part of a routine comprehensive metabolic panel or basic metabolic panel, or along with the blood urea nitrogen test whenever a doctor wants to evaluate the status of the kidneys." This sentence refers to several other tests that are different from a medical event of interest. Accordingly, such sentence may not be appropriate as an executive summary.

Still yet another exemplary feature that can cause the scorer component 118 to decrease a score assigned to a portion of text is when the phrasing of the portion of text is incorrect or inappropriate. An example of inappropriate phrasing is as follows: "Perform a kidney biopsy, which is done in some cases to check for a specific type of kidney disease, see how much kidney damage has occurred and help plan treatment."

Another exemplary feature that can cause the scorer component 118 to decrease a score assigned to a portion of text is when the portion of text includes excessive use of scientific terms (as determined by the natural language processor component 210) or through comparison of text in the portion of text with contents of a dictionary. For instance, the scorer component 118 can ascertain whether the portion of text being considered includes more than some threshold number of medical terms, where medical terms might be defined as terms whose frequency is much higher in medical literature that in layperson literature.

Yet another exemplary feature that can cause the scorer component 118 to decrease a score assigned to a portion of text is when the portion of text includes the use of what can be referred to as "high risk terms," wherein such terms are likely to cause concern to a patient when the patient looks up such terms. An exemplary sentence that includes such a high risk term can be as follows: "Sometimes it is important to know how much hCG is present to evaluate a suspected ectopic pregnancy or to monitor a woman following a miscarriage." Another exemplary sentence pertaining to such feature would be "Frequently miscarriages are monitored with quantitative blood hCG testing."

Still yet another exemplary feature that can cause the scorer component 118 to decrease a score assigned to a portion of text is when the portion of text cannot grammatically stand alone. An exemplary sentence they cannot grammatically stand alone is as follows: "The CBC test may be ordered by the doctor on a regular basis to monitor these conditions and drug treatments", since the sentence refers to "these conditions", such sentence cannot grammatically stand alone. It can be noted that this is different than the question of whether a sentence is grammatically complete.

Another exemplary feature that can cause the scorer component 118 to decrease a score assigned to a portion of text is when the name of a test or the name of a medical event of interest is reiterated. An exemplary sentence where a medical event is reiterated is as follows: "The Comprehensive Metabolic Panel checks your body's metabolism."

Yet another exemplary feature that can cause the scorer component 118 to decrease a score assigned to a portion of text is when the portion of text is not applicable to a current administration of the test being considered. This can also depend on the content of the EMR 104 of the patient. An example where a sentence is not applicable to the current administration of a test is as follows: "Because it is often ordered as a routine part of an annual physical examination or check up, over time the CMP provides an important baseline of a patient's basic physiology."

Still yet another exemplary feature that can cause the scorer component 118 to decrease a score assigned to a portion of text is when the portion of text refers to one part of a battery of tests of that are of interest to the individual or that are defined by the medical event, particularly when it is desirable to provide an explanation for an entire battery of tests. An exemplary sentence that refers to one part of a battery of tests is as follows: "The four electrolytes tests are carried out to check sodium, potassium, carbon dioxide, and chloride levels."

Another exemplary feature that can cause the scorer component 118 to decrease a score assigned to a portion of text is when the portion of text being considered refers to symptoms that the individual that corresponds to the EMR 104 is not experiencing. An example of this type of portion of text can be as follows: "when you have symptoms of a pancreatic disorder such as severe abdominal pain, fever, loss of appetite or nausea." This does not provide an accurate explanation for a medical event if the individual does not have the listed symptoms.

Another exemplary feature that can cause the scorer component 118 to decrease a score assigned to a portion of text is when the portion of text includes explanations of side effects of medications that the individual is not actually consuming. For instance, if the EMR 104 indicates that the individual 101 has been prescribed the medication DEXILANT, but has not been prescribed warfarin, then the following sentence may not be germane to the individual: "If you are taking DEXILANT with warfarin, you may need to be monitored because serious risks could occur."

Provided now is a list of features that can increase the score assigned by the scorer component 118 to a portion of text in the document 202 being analyzed by the scorer component 118. In other words, these features can indicate that the portion of text being considered may be a good executive summary (explanation) for a medical event. Again, these features are not absolute, but can be combined by the scorer component 118 to score and rank candidate portions of text in the document 202.

An exemplary feature that can cause the scorer component 118 to increase a score assigned to a portion of text is when the person of text being analyzed expands acronyms therein. Expansion of acronyms can indicate that the portion of text is attending to describe something in a manner that is understandable to lay persons.

Another exemplary feature that can cause the scorer component 118 to increase a score assigned to a portion of text is when the portion of text being considers draws a relationship to an organ system when such relationship is not obvious from the name of a lab or test. For instance, the phrase "to assess kidney function" would be assigned a relatively high score with respect to a medical event that does not indicate that kidney function is to be tested.

Yet another exemplary feature that can cause the scorer component 118 to increase a score assigned to a portion of text is when the portion of text mentions a method of administration, such as when a portion of text refers to for instance, a blood test, a urine test etc.

Still yet another exemplary feature that can cause the scorer component 118 to increase a score assigned to a portion of text is when such portion of text explains the fact that a test is in fact, a battery of many tests. For instance, the following sentence includes an explanation that a particular test is many tests: "A comprehensive metabolic panel is a group of 14 chemical tests that are done to determine the physiological condition of an individual."

Another exemplary feature that can cause the scorer component 118 to increase a score assigned to a portion of text is when the portion of text refers to symptoms that the patient is experiencing as evidenced in the EMR 104. For instance, if the EMR 104 indicated that the individual has experienced severe abdominal pain, the following phrase can be assigned a higher score: "When you have symptoms of a pancreatic disorder, such as severe abdominal pain, fever loss of appetite or nausea."

Still yet another exemplary feature that can cause the scorer component 118 to increase a score assigned to a portion of text is the portion of text is applicable to the medical history of the individual as evidenced in the EMR 104. For instance, the explanation "diabetics and others at risk for developing kidney disease may be monitored for small amounts of protein in their urine by performing a microalbumin test" would be applicable to a patient who has diabetes.

Other features that can be considered by the scorer component I 18 include whether or not portions of text mentioned symptoms, organs, systems or body parts, whether the portion of text being considered mentions problems or diagnoses, the length of a portion of text, a number words or characters in the portion of text, use of acronyms in medical terms in the portion of text, a number of medical terms in the portion of text, whether acronyms are defined in the portion of text, amongst other features.

Other data can also be considered by the scorer component 118 when assigning scores to portions of text as far as such portions of text ability to act as an executive summary for a medical event or an executive explanation for such medical event. These can include information that is specific to the individual including educational background of the individual, familiarity of the individual with medical terms, etc. For instance, a nurse may wish to have a different executive summary provided thereto for a medical event when compared to an explanation for the same medical event as desired by a schoolteacher. Thus, executive summaries can be generated for medical events in an EMR of an individual such that they are specified for such individual.

Figure 3:
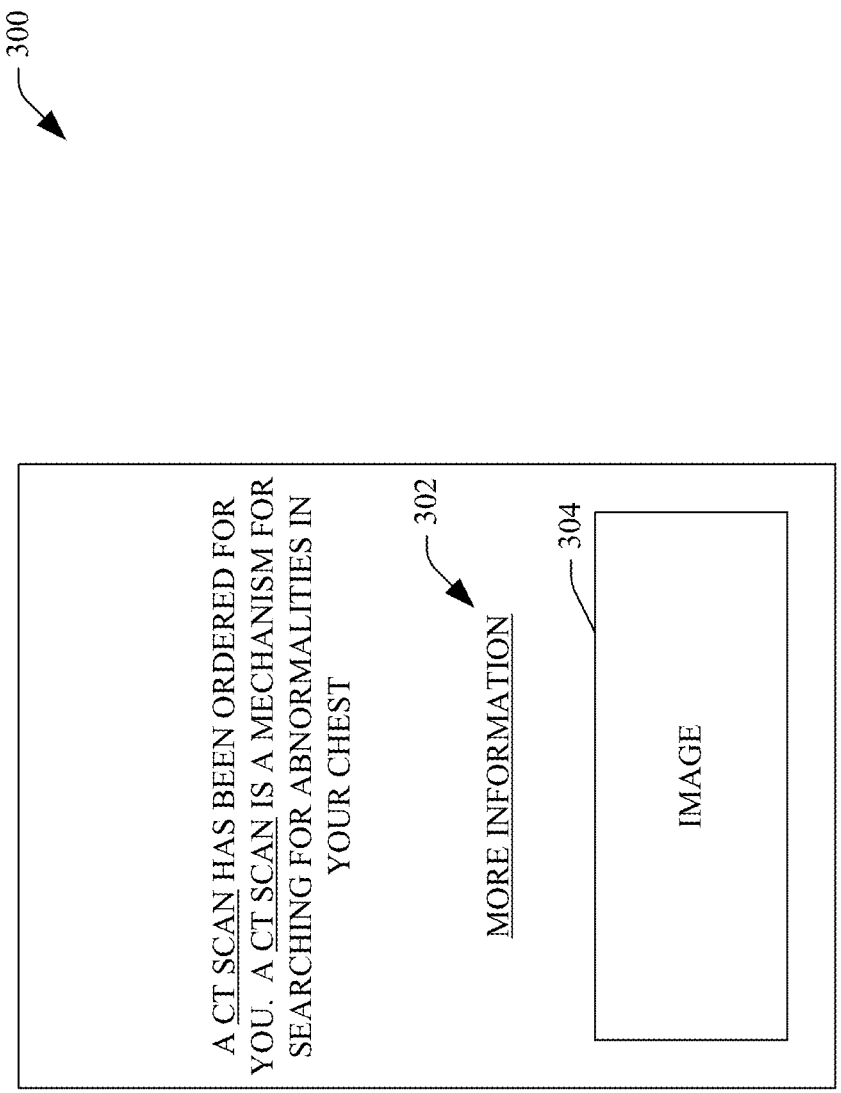
FIG. 3 is an exemplary graphical user interface for displaying a medical event and a corresponding executive summary to an individual.

With reference now to FIG. 3, am exemplary graphical user interface 300 that can depict a medical event in the EMR 104 of the individual together with an executive summary that is automatically extracted from a document is illustrated. The graphical user interface 300 includes text that identifies a medical event in the EMR 104 of the individual. In the exemplary graphical user interface 300, the medical event is a CT scan that has been ordered for the individual. As can be ascertained, the executive summary indicates that the CT scan is a mechanism for searching for abnormalities in the chest of the patient.

The graphical user interface 300 also includes a hyperlink that the individual can select to acquire additional information. For example, selection of such hyperlink 302 can cause a web browser to be directed to a web page from which the executive summary for the medical event has been extracted. Additionally or alternatively, the hyperlink 302 can point to a particular medical journal that describes medical events in detail. The exemplary graphical user interface 300 also includes an image 304 that pertains to the medical event. For instance, the image 304 can be retrieved from a database that includes images that are pre-associated with medical events. In another example, the image 304 can be automatically extracted from a web page from which the executive summary was extracted. In still yet another example, image analysis can be undertaken in connection with automatically selecting the image 304 to be displayed in the graphical user interface 300.

Figure 4:
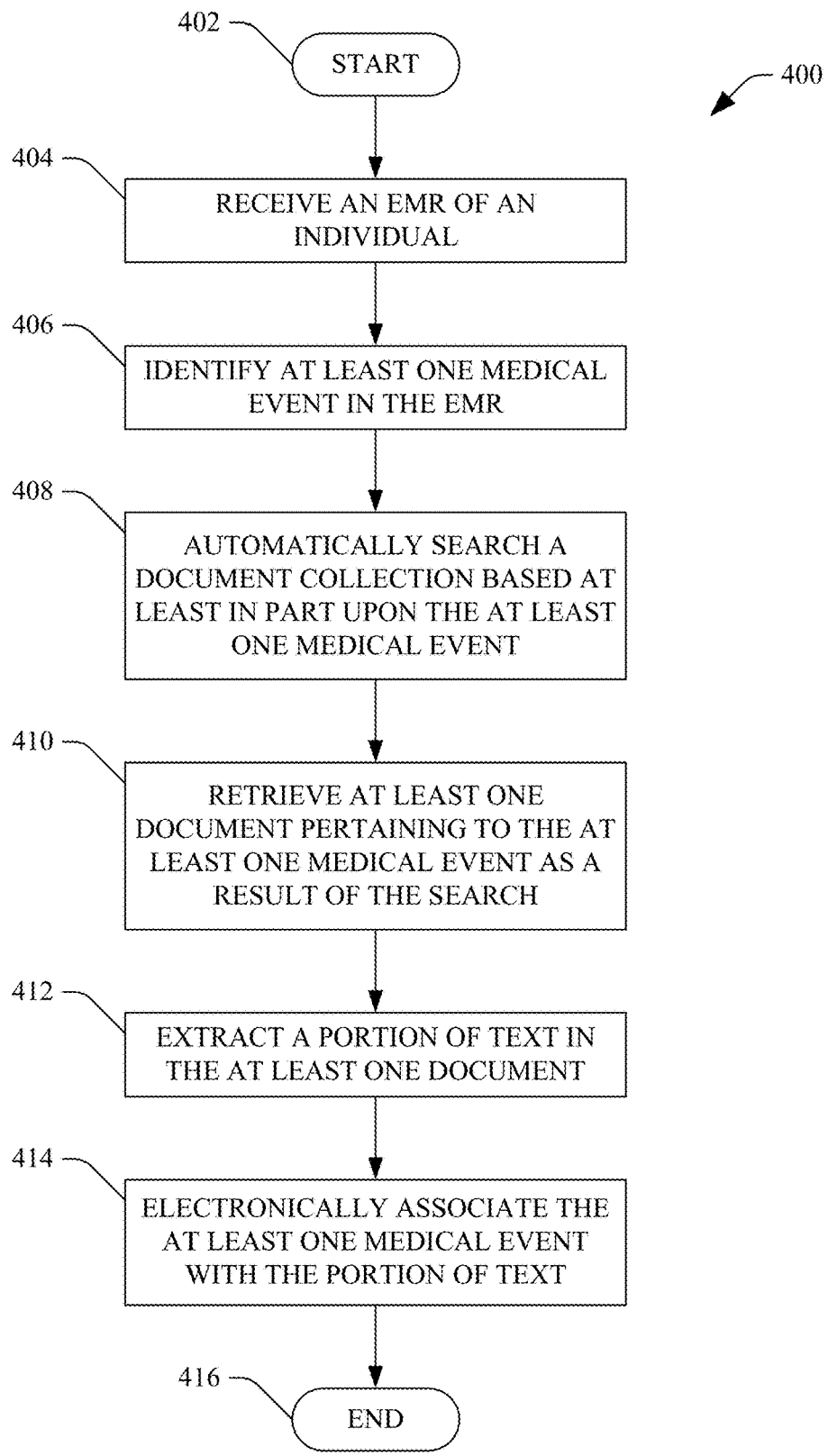
FIG. 4 is a flow diagram that illustrates an exemplary methodology for automatically generating an executive summary for a medical event included in an electronic medical record of an individual.
Figure 5:
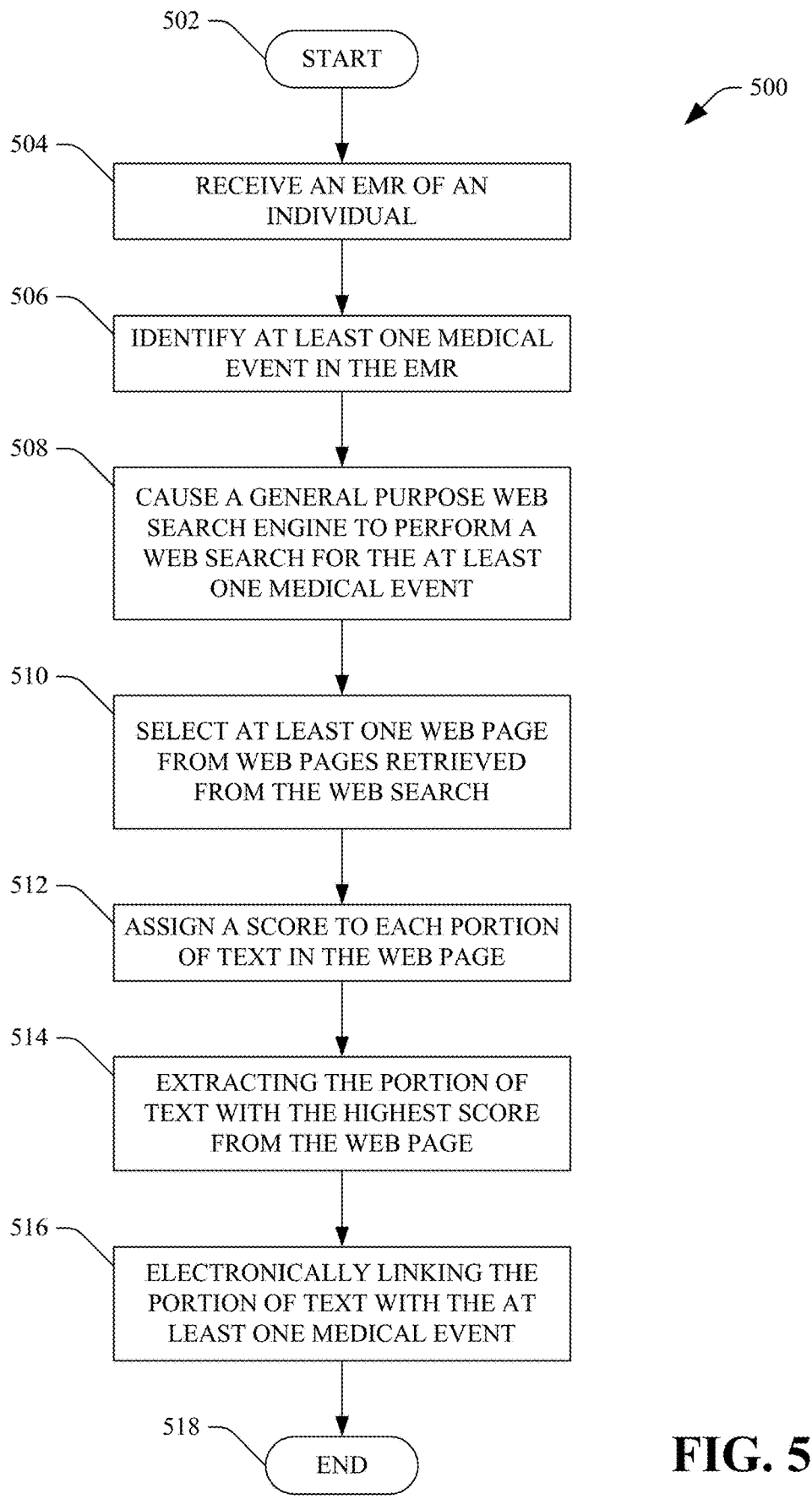
FIG. 5 is a flow diagram that illustrates an exemplary methodology for automatically generating an executive summary for a medical event in an electronic medical record of an individual.
Figure 6:
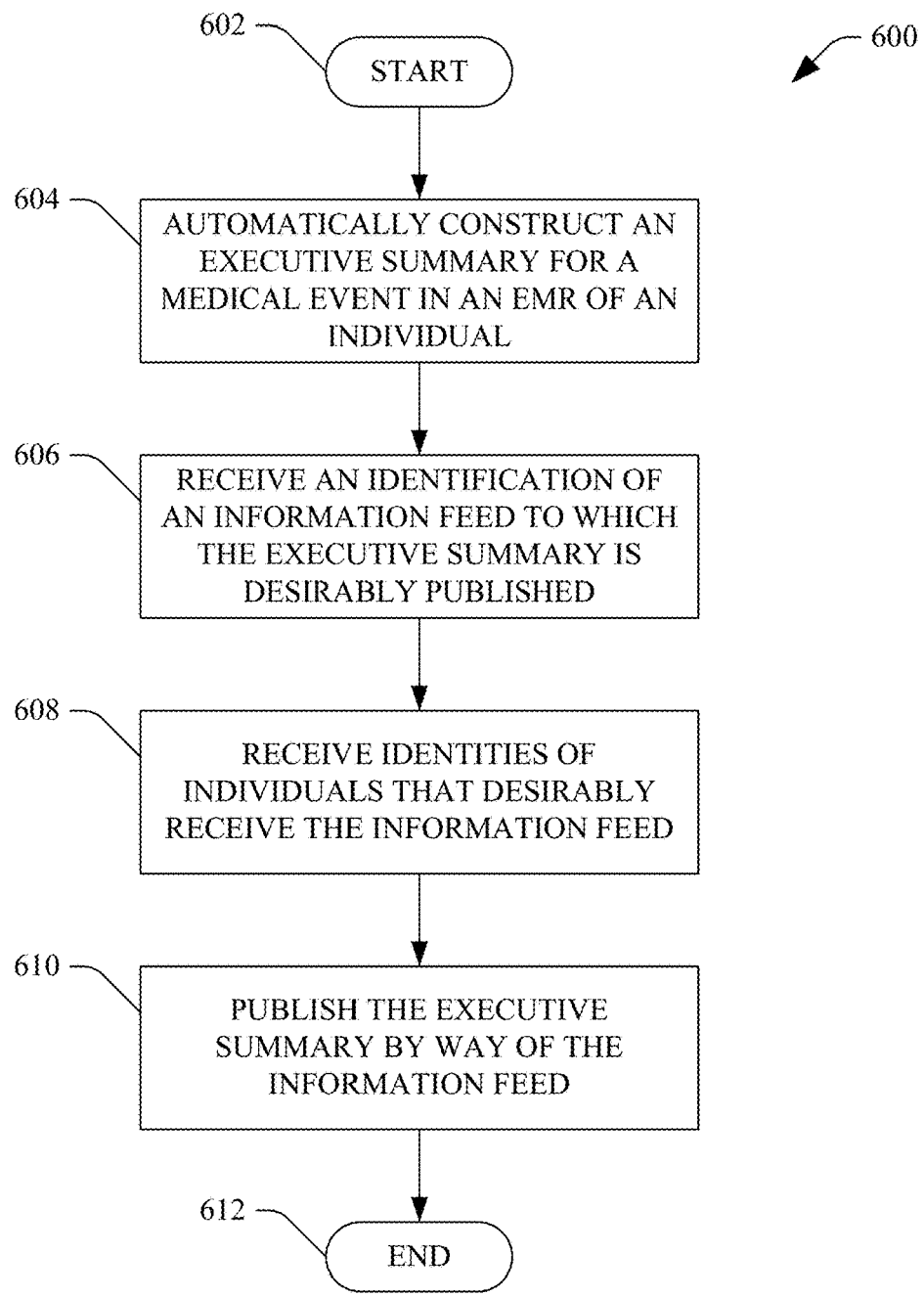
FIG. 6 is a flow diagram that illustrates an exemplary methodology for publishing an executive summary of a medical event in an electronic medical record of an individual to an information feed.

With reference now to FIGS. 4-6, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodologies may be stored in a computer-readable medium, displayed on a display device, and/or the like. The computer-readable medium may be a non-transitory medium, such as memory, hard drive, CD, DVD, flash drive, or the like.

Referring now to FIG. 4, a methodology 400 that facilitates automatically generating an executive summary or executive explanation for a medical event in an electronic medical record of an individual is illustrated. The methodology 400 begins at 402, and at 404 an EMR of an individual is received. The EMR comprises a plurality of medical events corresponding to the individual, such as tests ordered for the individual, medications prescribed to the individual, amongst other medical events.

At 406, at least one medical event from the plurality of medical events in the EMR is identified. For instance, content of the EMR can be compared with a predefined list of medical events, and at least one medical event can be identified in the EMR.

At 408, subsequently to identifying the at least one medical event, a document collection can be automatically searched based at least in part upon the at least one medical event. For instance, the least one medical event identified at 406 can be utilized as a search query, and the document collection can be searched over by a search mechanism utilizing such search query. In another example, a query can be generated based at least in part upon the identified medical event in the EMR.

At 410, at least one document is retrieved/located that pertains to the at least one medical event in the EMR as a result of searching the document collection. The at least one document retrieved from a document collection comprises a plurality of portions of text.

At 412, a portion of text is automatically extracted from the at least one document retrieved at 410. As has been described above, a portion of text can be extracted from the at least one document based at least in part upon other content in the EMR, explicitly provided user information, and/or features corresponding to a portion of text extracted from the at least one document. For instance, each portion of text in the at least one document can be assigned a score, and the portion of text extracted at 412 can be the portion of text in the document that has been assigned the highest score.

At 414, the at least one medical event is electronically associated with the portion of text extracted at 412. Thus, for instance, the individual may access the EMR, and the EMR may be modified to cause at least one medical event to have a hyperlink associated therewith. The individual may then select the hyperlink, which can cause a portion of text extracted at 412 be presented to the individual as an executive summary or explanation for the at least one medical event. Other delivery mechanisms have been described above, including but not limited to transmission of a text message to a mobile phone, publishing of the medical event and corresponding executive summary to an information feed, transmittal of the medical event together with the executive summary to an electronic account of another individual (such as an e-mail account), etc. The methodology 400 completes at 416.

With reference now to FIG. 5, an exemplary methodology 500 for automatically generating an executive summary/explanation for a medical event in an EMR of an individual is illustrated. The methodology 500 starts at 502, and at 504 an EMR of an individual is received. At 506, at least one medical event is identified in the EMR received at 504. Identification of medical events in EMRs has described above.

At 508, a general-purpose web search engine is caused to perform a web search based at least in part upon the at least one medical event identified at 506. For instance, the general-purpose web search engine can be provided with the at least one medical event and can utilize the at least one medical event as a query or portion of a query to perform a web search. As will be understood by one skilled in the art, the general-purpose web search engine will output a ranked list of search results (documents).

At 510, at least one web page is selected from web pages retrieved from performance of the search conducted at 508. The at least one web page can be selected at 510 based at least in part upon a position of the at least one web page in a ranked list of search results output by the general-purpose web search engine. In another example, a plurality of web pages can be selected at 510 based at least in part upon the position in the retrieved search results of the plurality of web pages. Thus, for instance, a top threshold number of web pages can be selected at 510. Further, each of the web pages selected 510 can include multiple portions of text.

At 512, scores are assigned to each portion of text in the at least one web page selected at 510. More specifically, scores are independently assigned to each separate portion of text in the at least one web page based at least in part upon, for instance, other medical events or data in the EMR of the individual, information explicitly provided by the individual, features of the portions of text in the web page, etc.

At 514, the portion of text in the web page that has been assigned the highest score amongst all scores assigned to portions of text in the web page is automatically extracted from such web page. This portion of text, for instance, can be the executive summary or description of the at least one medical event.

At 516, the portion of text is electronically linked with the at least one medical event. This association of the at least one medical event in the EMR of the individual with the portion of text that was automatically extracted from the at least one web page can allow the executive summary to be presented to the individual or others specified by the individual in a variety of manners, such as those that have been discussed above. The methodology 500 completes at 518.

Turning now to FIG. 6, an exemplary methodology 600 that facilitates publishing an executive summary/executive description of a medical event in an EMR of an individual is illustrated. The methodology 600 starts at 602, and at 604 an executive summary for a medical event in an EMR of an individual is automatically constructed. Such executive summary can be constructed, for instance, as described above.

At 606, an identification of an information feed to which the executive summary is desirably published is received. For instance, this information feed may be a social network feed of the individual, such that the executive summary and corresponding medical event from the EMR is published to an electronic account of the individual by way of such information feed.

At 608, identities of individuals that are desirably provided with the information feed are received. This allows the individual to specify friends and/or family whom individual wishes to share certain medical information, and further allows this information to be shared with the identified friends and/or family.

At 610, the executive summary is published by way of the information feed, and the methodology 600 completes at 612.

Figure 7:
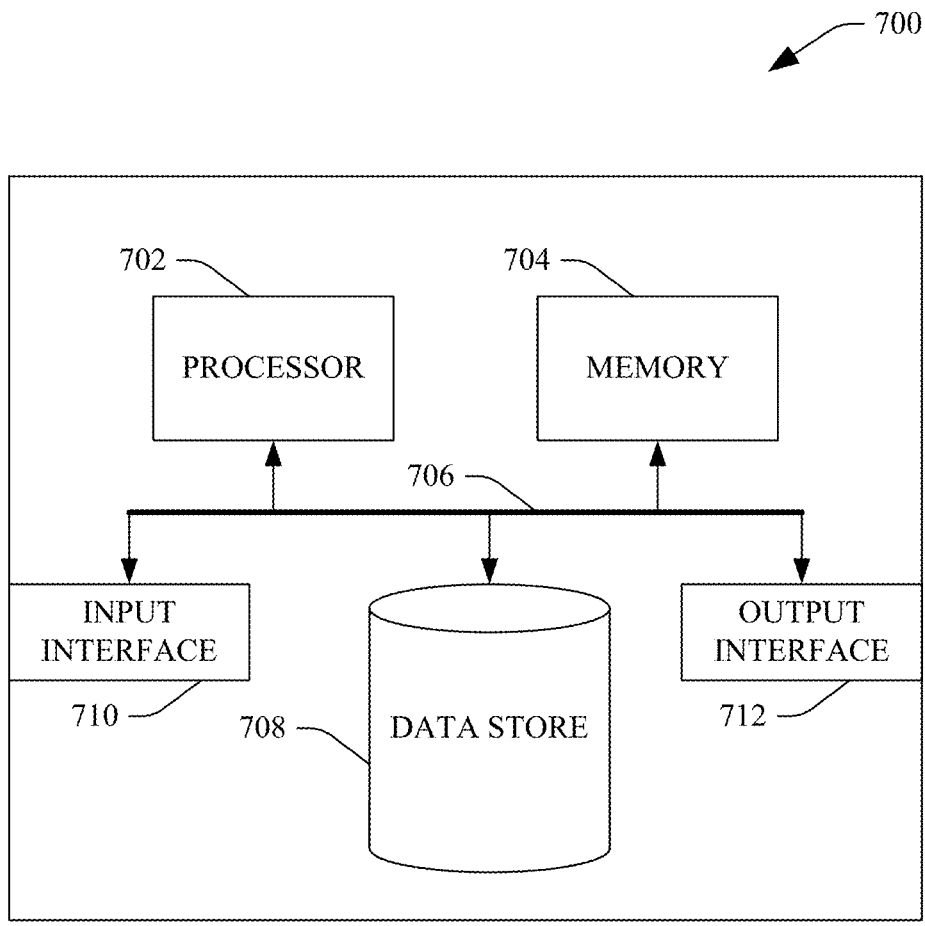
FIG. 7 is an exemplary computing system.

Now referring to FIG. 7, a high-level illustration of an exemplary computing device 700 that can be used in accordance with the systems and methodologies disclosed herein is illustrated. For instance, the computing device 700 may be used in a system that supports automatically generating an executive summary for a medical event in an electronic medical record of an individual. In another example, at least a portion of the computing device 700 may be used in a system that supports publishing an executive summary of a medical event in an EMR of an individual by way of an information feed. The computing device 700 includes at least one processor 702 that executes instructions that are stored in a memory 704. The memory 704 may be or include RAM, ROM, EEPROM, Flash memory, or other suitable memory. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store EMRs, documents, lists of predefined medical events, etc.

The computing device 700 additionally includes a data store 708 that is accessible by the processor 702 by way of the system bus 706. The data store may be or include any suitable computer-readable storage, including a hard disk, memory, etc. The data store 708 may include executable instructions, searchable documents, EMRs, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

Additionally, while illustrated as a single system, it is to be understood that the computing device 700 may be a distributed system. Thus, for instance, several devices may be in communication by way of a network connection and may collectively perform tasks described as being performed by the computing device 700.

As used herein, the terms "component" and "system" are intended to encompass hardware, software, or a combination of hardware and software. Thus, for example, a system or component may be a process, a process executing on a processor, or a processor. Additionally, a component or system may be localized on a single device or distributed across several devices. Furthermore, a component or system may refer to a portion of memory and/or a series of transistors.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A computing system comprising:
a processor; and
memory storing instructions that, when executed by the processor, cause the processor to perform acts comprising:
receiving an electronic medical record (EMR) for a patient, wherein the EMR includes a reference to a medical event with respect to the patient;
responsive to receiving the EMR for the patient, identifying the medical event in the EMR;
responsive to identifying the medical event in the EMR, identifying a document from a document corpus based upon the medical event, wherein the document is external to the EMR and comprises content;
constructing an executive summary for the medical event based upon the document, wherein the executive summary for the medical event comprises the content from the document;
responsive to constructing the executive summary for the medical event, updating the EMR for the patient to include the executive summary for the medical event, wherein updating the EMR for the patient to include the executive summary for the medical event comprises updating the EMR to include a selectable graphical element that corresponds to the medical event, wherein the executive summary for the medical event is presented responsive to the selectable graphical element being selected; and
transmitting the EMR for the patient to a client computing device for viewing by the patient, wherein the EMR includes the executive summary for the medical event.

2. The computing system of claim 1, wherein the medical event referenced in the EMR is one of:
a test that has been performed on the patient;
a disease with which the patient has been diagnosed;
a medication prescribed to the patient; or
a treatment that has been performed on the patient.

3. The computing system of claim 1, wherein identifying the document from the document corpus comprises:
using the medical event as a query, searching over the document corpus, wherein searching over the document corpus results in generation of search results, the search results comprise a ranked list of search results, wherein the document is a most highly ranked document in the ranked list of search results.

4. The computing system of claim 3, wherein searching over the document corpus is performed by a general purpose search engine.

5. The computing system of claim 3, wherein the document corpus is the World Wide Web, and further wherein the document is a web page.

6. The computing system of claim 1, wherein constructing the executive summary for the medical event based upon the document comprises:
identifying a portion of text in the document, wherein the portion of text comprises the content;
assigning a score to the portion of text; and
including the content in the executive summary for the medical event based upon the score assigned to the portion of text.

7. The computing system of claim 6, wherein constructing the executive summary for the medical event based upon the document further comprises:
identifying several portions of text in the document;
assigning a score to each portion of text in the portions of text in the document, wherein the score assigned to the portion of text is a highest score from amongst all scores assigned to the several portions of text in the document; and
including the content in the executive summary for the medical event based upon the score assigned to the portion of text being the highest score from amongst all the scores assigned to the several portions of text in the document.

8. The computing system of claim 1, wherein the EMR for the patient comprises reference to a second medical event, and further wherein the document is identified from the document corpus based upon the second medical event being referenced in the EMR for the patient.

9. The computing system of claim 1, wherein the selectable graphical element is a hyperlink for the medical event.

10. The computing system of claim 1, wherein the client computing device is a mobile telephone of the patient.

11. A method executed by one or more processors of a computing system, the method comprising:
receiving an electronic medical record (EMR) for a patient, wherein the EMR includes a reference to a medical event with respect to the patient;
responsive to receiving the EMR for the patient, identifying the medical event in the EMR;
responsive to identifying the medical event in the EMR, identifying a document from a document corpus based upon the medical event, wherein the document is external to the EMR and comprises content;
constructing an executive summary for the medical event based upon the document, wherein the executive summary for the medical event comprises the content from the document;
responsive to constructing the executive summary for the medical event, updating the EMR for the patient to include the executive summary for the medical event, wherein updating the EMR for the patient to include the executive summary for the medical event comprises updating the EMR to include a selectable graphical element that corresponds to the medical event, wherein the executive summary for the medical event is presented responsive to the selectable graphical element being selected; and transmitting the EMR for the patient to a client computing device for viewing by the patient, wherein the EMR includes the executive summary for the medical event.

12. The method of claim 11, wherein the medical event referenced in the EMR is one of:
a test that has been performed on the patient;
a disease with which the patient has been diagnosed;
a medication prescribed to the patient; or
a treatment that has been performed on the patient.

13. The method of claim 11, wherein identifying the document from the document corpus comprises:
using the medical event as a query, searching over the document corpus, wherein searching over the document corpus results in generation of search results, the search results comprise a ranked list of search results, wherein the document is a most highly ranked document in the ranked list of search results.

14. The method of claim 13, wherein searching over the document corpus is performed by a general purpose search engine.

15. The method of claim 13, wherein the document corpus is the World Wide Web, and further wherein the document is a web page.

16. The method of claim 11, wherein constructing the executive summary for the medical event based upon the document comprises:
identifying a portion of text in the document, wherein the portion of text comprises the content;
assigning a score to the portion of text; and
including the content in the executive summary for the medical event based upon the score assigned to the portion of text.

17. The method of claim 16, wherein constructing the executive summary for the medical event based upon the document further comprises:
identifying several portions of text in the document;
assigning a score to each portion of text in the portions of text in the document, wherein the score assigned to the portion of text is a highest score from amongst all scores assigned to the several portions of text in the document; and
including the content in the executive summary for the medical event based upon the score assigned to the portion of text being the highest score from amongst all the scores assigned to the several portions of text in the document.

18. The method of claim 11, wherein the EMR for the patient comprises reference to a second medical event, and further wherein the document is identified from the document corpus based upon the second medical event being referenced in the EMR for the patient.

19. The method of claim 11, wherein the selectable graphical element is a hyperlink for the medical event.

20. A computer-readable memory device comprising instructions that, when executed by a processor, cause the processor to perform acts comprising:
receiving an electronic medical record (EMR) for a patient, wherein the EMR includes a reference to a medical event with respect to the patient;
responsive to receiving the EMR for the patient, identifying the medical event in the EMR;
responsive to identifying the medical event in the EMR, identifying a document from a document corpus based upon the medical event, wherein the document is external to the EMR and comprises content;
constructing an executive summary for the medical event based upon the document, wherein the executive summary for the medical event comprises the content from the document;
responsive to constructing the executive summary for the medical event, updating the EMR for the patient to include the executive summary for the medical event, wherein updating the EMR for the patient to include the executive summary for the medical event comprises updating the EMR to include a selectable graphical element that corresponds to the medical event, wherein the executive summary for the medical event is presented responsive to the selectable graphical element being selected; and
transmitting the EMR for the patient to a client computing device for viewing by the patient, wherein the EMR includes the executive summary for the medical event.

* * * * *